United States Patent [19]

Hamilton

[11] Patent Number: 4,471,662
[45] Date of Patent: Sep. 18, 1984

[54] NON-DESTRUCTIVE DOOR FRAME TESTER

[76] Inventor: William J. Hamilton, 1180 Woodroffe Ave., Ottawa, Ontario, Canada, K2C 2T3

[21] Appl. No.: 452,778

[22] Filed: Dec. 23, 1982

[51] Int. Cl.³ ............................................. G01N 3/00
[52] U.S. Cl. ...................................... 73/788; 73/789
[58] Field of Search ......................... 73/788, 789, 849

[56] References Cited

U.S. PATENT DOCUMENTS 169,376 11/1875 Scott ..................................... 73/789
184,830 11/1876 Brown .................................. 73/789

Primary Examiner—Anthony V. Ciarlante
Attorney, Agent, or Firm—W. Charles Kent; William R. Edgar

[57] ABSTRACT

Apparatus for testing strength of door frames, consisting of a sturdy set of relatively movable pressure plates made of a heavy gauge sheet metal, designed for easy insertion into the usual space between the door and frame jamb at a position directly above the area of the latch bolt, and an interconnecting drive mechanism to apply a balanced force between the door and the frame on the inside only. Energy to drive the mechanism is supplied by the operator, using an ordinary drive socket and torque wrench with a modified scale that provides a direct indication of the force generated at the pressure plates. Frame spreading is also read on another scale and indicates an inverse measure frame strength. Rotary motion from the wrench is converted to linear motion of the plates by means of a lever assembly which also multiplies the driving force to the high level required. This door frame tester provides the user with an accurate high strength means for non-destuctive testing of new and older door frames.

10 Claims, 7 Drawing Figures

FIG.1
FIG.2
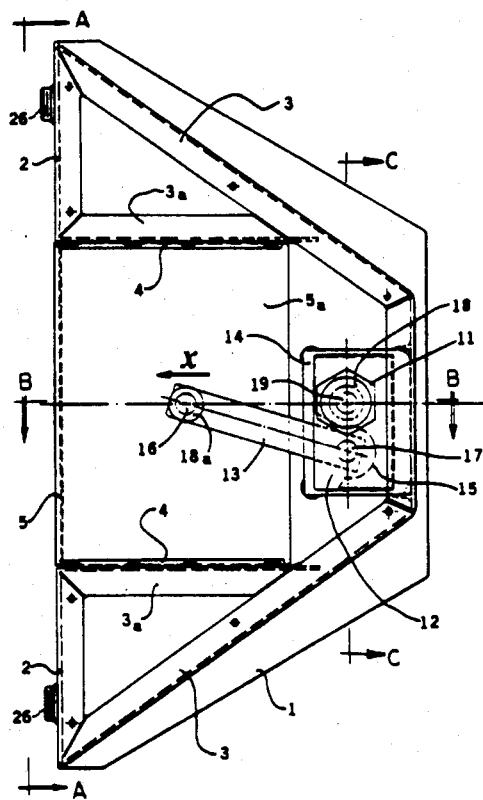
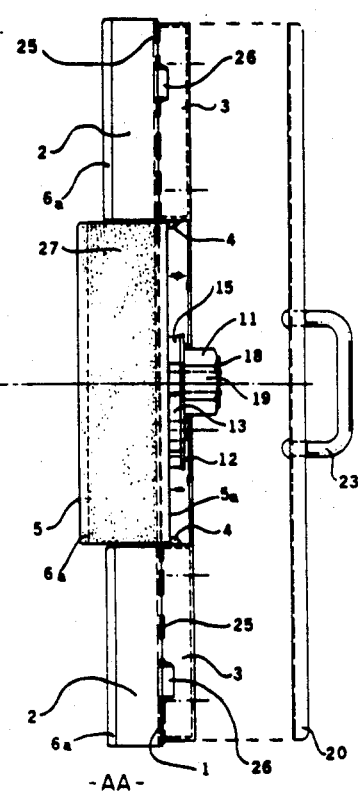
FIG.3
FIG.3a
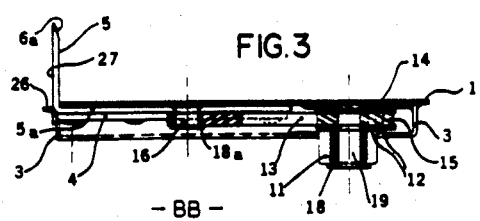
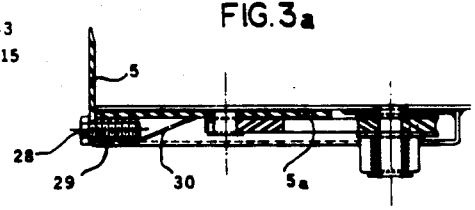

NON-DESTRUCTIVE DOOR FRAME TESTER

BACKGROUND OF THE INVENTION

This invention relates to an apparatus and method for non-destructive testing of the strength of door frames, and appertains particularly to a mechanism designed to indicate frame strength by a method which measures the spreading effect of a known force against the frame.

Burglars often gain entry to a building or room in a building through a doorway by applying a spreading force to the frame of a door in the vicinity of the doorknob, until the latch bolt is freed from engagement with its corresponding strike plate in the door jamb. There has been little in the way of testing apparatus or procedures for checking entrance door security relative to the strength of the mounted frame.

While there are many prior art devices in general use for grading lumber that measure the stiffness or strength of the lumber, none of such devices would be suitable for testing the strength of door frames in the field. Therefore an efficient measurement device for checking a door frame's effective resistance to a spreading force would have obvious advantages and applications, particularly if it were portable.

Accordingly it is an object of the present invention to provide a device for testing the strength of door frames. It is a further object to provide a testing device and method which can be controlled and will not destroy or damage the door and door frame being tested.

SUMMARY OF THE INVENTION

The apparatus according to the present invention comprises a set of flat pressure plates to be inserted for operation in the usual clearance space between the latch side edge of a closed door and the facing frame jamb. The plates are relatively movable with respect to each other between retracted position with the plates aligned in the same plane and non-aligned, testing position with the plates parallel but linearly spaced in different planes from each other and bearing against the latch side edge of the door and the frame jamb. Means are provided to effect relative linear movement of the plates preferably in a direction normal to their planes, between retracted and non-aligned positions. The apparatus also provides means to measure the force exerted by the plates on the door and door frame jamb when the plates are in non-aligned testing position. In a preferred embodiment of the apparatus according to the present invention, a means is provided to measure simultaneously the degree of spreading of the frame jamb when the plates are in non-aligned testing position.

According to the invention there is also provided a process for non-destructive, on site testing of the strength of door frames. A known spreading force is applied between the latch side edge of a closed door and the facing frame jamb, in the vicinity of the door latch, and the frame jamb deflection is measured as a function of that spreading force.

The apparatus and method according to the present invention provide an inexpensive, non-destructive way of on site testing of the strength of door frames.

BRIEF DESCRIPTION OF THE DRAWINGS

Other objects and advantages of the invention will become apparent upon reading the following detailed description and upon referring to the drawings in which:

FIG. 1 is a front elevation of an example embodiment of a tester device according to the present invention with cover plate removed to expose the moving parts, and illustrates the main plate and body structure;

FIG. 2 is an end view in the direction—AA—of FIG. 1, with the cover plate shown separately;

FIG. 3 is a sectional view taken through—BB—of FIG. 1, to show all of the parts;

FIG. 3a is a sectional view of an alternative embodiment of tester device according to the present invention with a removable pressure plate;

Figure 4:
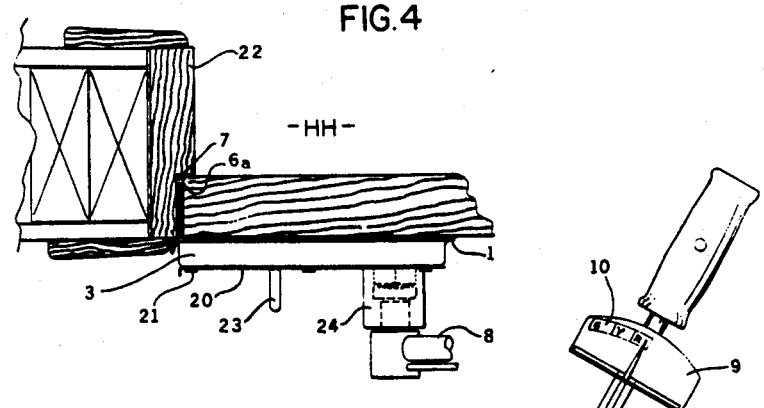
FIG. 4 is a sectional view taken through—HH—of FIG. 6, to show the tester in place in the usual door and frame structure, ready for operation.

While the invention will be described in connection with example embodiments it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE INVENTION

Turning to the drawings there is shown in FIGS. 1 and 2 an example embodiment of the tester device according to the present invention, comprising a main body mounting plate 1 having pressure plates 2 formed from the same plate by bending to 90°. Between pressure plates 2 is positioned movable pressure plate 5 as part of mechanical slide plate 5a. Mechanical slide plate 5a is linked by a connecting rod 13 and pins 16 and 17 to a drive mechanism consisting of lever assembly parts 11, 12 and 19 secured to plate 1. Movable pressure plate 5 is preferably provided with a roughened external surface 27 to prevent slippage on the door jamb while the device is being used. The bed for mechanical slide plate 5a is also the same main body plate 1, which is an integral part of the main body assembly comprised of plate 1 and plates 2, intermediate frame structure 3 and guide bars 4. The intermediate frame structure 3 and guide bars 4 are made integral with the main body plate 1 by welded construction. Movable plate 5, when in the retracted position as shown in the drawings, is aligned between the two pressure plates 2, in the same vertical plane.

As can be seen in FIGS. 2 and 4, leading edge 6a of pressure plates 2 and movable plate 5 is tapered to facilitate easier entry into a narrower than usual door-to-frame space 7. Also edge 6a of movable plate 5 extends beyond the leading edges 6a of pressure plates 2 a sufficient distance to ensure that the device is used only from inside a door and door frame, thus preventing the device from being used as a burglar's tool from outside. This can be done by making the width of the intermediate plate greater than that of the outer pressure plates by a dimension which is slightly greater than the usual door stop thickness.

Figure 6:
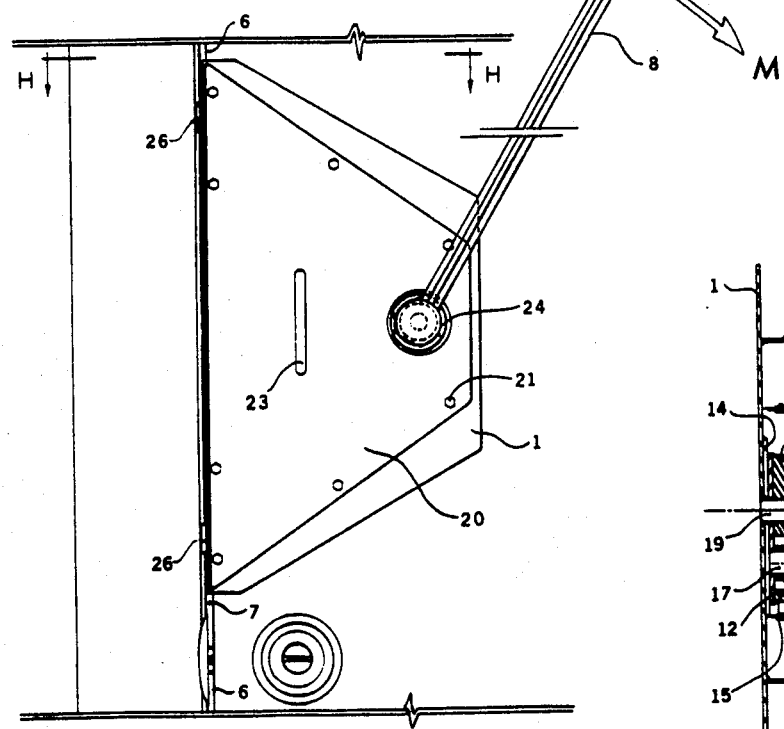
FIG. 6 is a front elevation including the complete tester assembly of FIG. 1, showing the device together with its torque wrench and a modified indicating scale.
Figure 5:
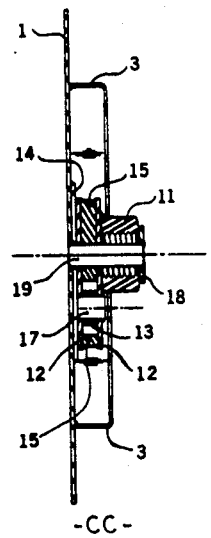
FIG. 5 is a section view through—CC—of FIG. 1.

Intermediate frame structure 3 adds strength to the main body plate assembly and reinforces pressure plates 2 by means of intermittant welding at 25 (FIG. 2). Intermediate frame structure 3 also serves as a mounting surface for cover plate 20. Guide bars 4 are welded to the intermediate frame arms 3a and, together with mechanical slide plate 5a and main body plate 1, form a machine slide assembly of adequate strength to control the movement of pressure plate 5. On final assembly, cover plate 20 is located on intermediate mounting frame 3 and held in place by fasteners 21 (FIG. 6). This plate also adds strength to the vertical coordinate of the main body plate 1 and serves as a mounting plate for lifting handle 23.

Mechanical slide plate 5a is moved by means of a lever assembly and activated by the operator using a torque wrench 8 and drive socket 24. The components of the lever assembly include lever drive nut 11, slide plates 12, connecting rod 13, intermediate spacer plate 15, connecting rod pin 17 and lever assembly mounting pin 19 (FIGS. 1, 2, 3 and 5). Lever drive nut 11 is welded to the lever assembly and rotates on mounting pin 19 (FIG. 3) which is also welded to the main body mounting plate 1. Components 11, 12, 13 and 17 of the lever mechanism are assembled by welded construction and connecting rod 13 is made captive of this assembly. Retaining washers 18 and 18a can be welded as shown to pins 19 and 16 or other suitable retaining washers used for easier removal of the lever assembly. Spacer plate 14, is of a thickness to laterally position the lever assembly for proper alignment of connecting rod 13 against slide plate 5a. It also adds support for mounting pin 19. The lever assembly and mechanical slide provide a complete transmission circuit for energy from the operator to the intermediate pressure plate 5. The high level of force generated between the pressure plates 2 and 5 is derived from the short lever length and shown in FIG. 1 as the dimension between mounting pin 19 and connecting rod pin 17.

An alternative mechanical structure as shown in FIG. 3a can also provide for a removable pressure plate 5 connected by way of mounting bar 29 and cap screws 28 to slide plate 5a, in order to allow for interchangeability or replacement.

Scale plates 26 may be located approximately as shown in FIGS. 1 and 2, extending from the intermediate frame 3. These scale plates may be graduated for example in 1/16 inch units and are short in length to serve as limit indicators for the maximum allowable opening of the door-to-frame space observed during testing. Also scale plate 9 of an ordinary torque wrench is modified by applying a pressure sensitive label which may have coloured segments to indicate pressure ranges as shown at 10, or a label with a scale calibrated with pounds of force, to indicate directly the actual force applied against the frame.

Use of the frame tester involves the use of lifting handle 23 to position and direct pressure plates 2 and 5 (with pressure plate 5 fully retracted as shown in FIG. 1) into vertical alignment with door clearance space 7 and inserting these plates forward into space 7 until the under surface of main body plate 1 rests flat against the door as shown in FIGS. 4 and 6, preferably above the area of the latch bolt. In this position and with drive socket 24 and torque wrench 8 fitted on drive nut 11, the tester is ready to be energized. Holding the tester in this position and with torque wrench 8 attached as shown in FIG. 6, a light pressure is applied to the wrench in direction M until pressure plates 5 and 2 engage the frame jamb and door's edge 6 respectively. Rotation of torque wrench 8 in direction M about lever drive nut 11 (FIG. 6) causes energy to be transmitted through the lever and linearly move mechanical slide plate 5a and pressure plate 5 in direction X or outwardly as shown in FIG. 1 into contact with the frame jamb. The test actually begins at this point. Increasing the rotary drive to the torque wrench in direction M will move the door and frame jamb apart by a measure which will depend on the resistance of the frame at both sides of the doorway, the strength of the wood in the frame and the level of force applied. Since a common round latch bolt extends from the door's edge approximately 7/16 inches, the maximum allowable door-to-frame opening due to testing should be limited to 5/16 inches. Even this amount of flexing or opening would indicate a need to make some adjustment in order that an excessive opening dimension be limited or reduced.

Also, the level of force as shown by the scale on the torque wrench when taken in conjunction with the dimension of space produced by the tester as read from scale plate 26, can serve to derive a figure of merit which is simply a ratio of the force applied to the dimension of the opening (of the door-to-frame space produced by that force) in inches. For example, a strong frame and door assembly might allow an opening of only 3/16 inches (0.1875 inches) even at 1800 pounds of force. Accordingly, the figure of merit would be equal to 1800/0.1875 or 9600. On the other hand an opening of ¼ inches with only 800 lbs. applied would yield a figure of 3200. Consequently, for a dimensional limit of 5/16 inches and a frame tester force range of 2000 pounds, the minimum acceptable figure of merit would be 6400. However, 6400 is only a minimum figure of merit that might be derived from a test that produced an opening of ⅛ inches, with a force level of 800 pounds—a pressure level much too low, since burglar tools can produce pressure levels that can reach 2000 pounds to spread door frames.

Therefore a meaningful evaluation of the mounted door and frame for strength in the area of the latch bolt should depend on two measurements, and both are available from the frame tester scales 26 and 10; the increased door-to-frame space as produced by pressure plates 2 and 5; and a specific level of door frame resistance (as indicated on torque wrench scale 10) to be expected from any properly reinforced door frame as a minimum strength requirement.

It will be understood that the use of spaced pressure plates 2 in conjunction with movable pressure plate 5 transmits a balanced force to produce an equal and opposite reaction between door and frame, with no twisting or lateral motion allowed. The tester according to the present invention thus provides a means for the operator or bystander to read directly the actual stress level being applied and the measure of frame deflection during testing. Furthermore since an operator will normally sense and observe the magnitude of physical effects produced by the applied force acting between the door and frame jamb, the testing force can be controlled and limited (to prevent damage or destruction) to any level which demonstrates an obvious structural weakness, by failing to resist the testing force, and by allowing a large opening to develop between the door and frame jamb at relatively low pressure levels. The pressure plates are also provided with an adequate surface area to prevent deforming the wood of either the door or frame jamb.

The tester according to the present invention thus provides a small low-cost testing device that may be carried in an attache case as a field testing unit. The measurement facility, and the method of testing further provide a direct quantitive indication of the strength level in the mounted door frame, and, as previously explained, allow the derivation of a numerical value of frame strength of the installed frame structure by comparing the resistance of that structure to the overall door-to frame space produced under test.

Thus there has been provided in accordance with the present invention, an apparatus for testing strength of door frames in housing, that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What I claim as my invention:

1. Apparatus for non-destructive on site testing of the strength of door frames comprising:
   (a) a sturdy set of flat pressure plates to be inserted for operation in the usual clearance space on the inside between the latch side edge of a closed door and the facing frame jamb, the plates being relatively movable with respect to each other between retracted position with the plates aligned in the same plane and non-aligned, testing position with the plates parallel but linearly spaced in different planes from each other and bearing against the latch side edge of the door and the frame jamb;
   (b) means to effect relative linear movement of the plates between aligned and non-aligned positions; and
   (c) means to measure the force exerted by the plates on the door and frame jamb when the plates are in non-aligned testing position.

2. Apparatus according to claim 1 wherein the plates are relatively linearly movable in a direction normal to the respective planes.

3. Apparatus according to claim 2 further comprising:
   (d) means to measure simultaneously the degree of spreading of the frame jamb when the plates are in non-aligned testing position.

4. Apparatus according to claim 3 wherein the means to measure the degree of spreading of the frame jamb during testing comprises a scale plate secured to the apparatus to extend across the clearance space between the door edge and frame jamb and measure the increase in width of this space.

5. Apparatus according to claim 1 wherein the set of pressure plates comprises the combination of an intermediate movable pressure plate and two stationary coplanar outer plates attached to a main body assembly, the intermediate plate being aligned when retracted into the same plane as the outer plates.

6. Apparatus according to claim 5 wherein the width of the intermediate plate is greater than that of the outer pressure plates by a dimension which is slightly greater than the usual door stop thickness to restrict the use of the apparatus on the outside of the door and door frame.

7. Apparatus according to claim 5 wherein the intermediate plate is positioned with respect to the outer plates so that a balanced force is applied between the door and frame jamb when the plates are in non-aligned testing position.

8. Apparatus according to claim 7 wherein the intermediate plate is secured to a mechanical slide means movably associated with the main body assembly, the mechanical slide mechanically associated with the means to effect linear reciprocating movement of the intermediate plate.

9. Apparatus according to claim 5 wherein the means to effect linear movement of the intermediate plate comprises linkage means connecting the intermediate plate to a lever assembly that is rotatably secured to the main body assembly to effect movement of the intermediate plate, actuation means being secured to the lever assembly and exposed for use by an operator of the apparatus.

10. Apparatus according to claim 9 wherein the lever actuation means comprises a lever drive nut for connection by means of a drive socket to a torque wrench, the torque wrench being provided with a scale to measure the reaction of the frame jamb to the spreading force transmitted by the pressure plates.

* * * * *